(12) United States Patent
Obata et al.

(10) Patent No.: US 9,880,236 B2
(45) Date of Patent: Jan. 30, 2018

(54) PET-MRI APPARATUS

(71) Applicants: National Institute of Radiological Sciences, Chiba-shi, Chiba (JP); Toshiba Medical Systems Corporation, Tochigi (JP)

(72) Inventors: Takayuki Obata, Chiba (JP); Taiga Yamaya, Chiba (JP); Iwao Kanno, Chiba (JP); Hitoshi Yamagata, Otawara (JP); Takuzo Takayama, Utsunomiya (JP); Kazuya Okamoto, Saitama (JP)

(73) Assignees: National Institute for Quantum and Radiological Science and Technology, Chiba (JP); Toshiba Medical Systems Corporation, Otawara-shi, Tochigi (JP)

( * ) Notice: Subject to any disclaimer, the term of this patent is extended or adjusted under 35 U.S.C. 154(b) by 1300 days.

(21) Appl. No.: 13/874,795

(22) Filed: May 1, 2013

(65) Prior Publication Data

US 2013/0241555 A1    Sep. 19, 2013

Related U.S. Application Data

(63) Continuation of application No. PCT/JP2011/074991, filed on Oct. 28, 2011.

(30) Foreign Application Priority Data

Nov. 1, 2010    (JP) .................................. 2010-245606

(51) Int. Cl.
*G01R 33/28*    (2006.01)
*A61B 6/03*    (2006.01)
(Continued)

(52) U.S. Cl.
CPC .............. *G01R 33/28* (2013.01); *A61B 6/037* (2013.01); *A61B 6/4417* (2013.01);
(Continued)

(58) Field of Classification Search
CPC .. G01R 33/422; G01R 33/481; A61B 5/0035; A61B 5/055; A61B 6/5247; A61B 6/5235; A61B 6/4417; A61B 6/037; G01T 1/1603

See application file for complete search history.

(56) References Cited

U.S. PATENT DOCUMENTS 5,384,536 A    1/1995 Murakami et al.
7,323,874 B2 *    1/2008 Krieg .................... G01T 1/1603
                                                      324/318

(Continued)

FOREIGN PATENT DOCUMENTS

CN    101322042 A    12/2008
JP    5-261083    10/1993
(Continued)

OTHER PUBLICATIONS

Extended European Search Report dated Nov. 28, 2016 in EP 11837955.1.

(Continued)

*Primary Examiner* — Dixomara Vargas
(74) *Attorney, Agent, or Firm* — Nixon & Vanderhye P.C.

(57) ABSTRACT

In a PET (Positron Emission Tomography)-MRI (Magnetic Resonance Imaging) apparatus of an embodiment, a magnet that is a seamless structure generates a static magnetic field in a bore having a cylindrical shape. First detectors and second detectors are each formed in a ring shape and detect gamma rays emitted from positron emitting radionuclides injected into a subject. The first detectors and the second detectors are disposed with a space therebetween in an axial direction of the bore so as to interpose the magnetic field center of the static magnetic field therebetween.

15 Claims, 6 Drawing Sheets

(51) Int. Cl.
*A61B 6/00* (2006.01)
*G01R 33/48* (2006.01)
*G01T 1/16* (2006.01)
*A61B 5/00* (2006.01)
*A61B 5/055* (2006.01)

(52) U.S. Cl.
CPC .......... *G01R 33/481* (2013.01); *G01T 1/1603* (2013.01); *A61B 5/0035* (2013.01); *A61B 5/055* (2013.01)

(56) References Cited

U.S. PATENT DOCUMENTS

| | | | |
|---|---|---|---|
| 7,667,457 B2 | 2/2010 | Linz et al. | |
| 7,945,079 B2 * | 5/2011 | Rosen | G06T 11/005 382/107 |
| 8,064,981 B2 * | 11/2011 | Eberler | G01R 33/28 600/407 |
| 8,131,340 B2 * | 3/2012 | Eberlein | G01R 33/34046 600/407 |
| 8,467,847 B2 * | 6/2013 | Caruba | A61B 5/0035 600/411 |
| 8,594,404 B2 | 11/2013 | Yamaya et al. | |
| 8,706,189 B2 * | 4/2014 | Hagen | A61B 5/0555 128/869 |
| 9,063,203 B2 * | 6/2015 | Martin | A61B 6/037 |
| 9,495,771 B2 * | 11/2016 | El Fakhri | G06T 11/005 |
| 9,498,167 B2 * | 11/2016 | Mostafavi | A61B 6/032 |
| 9,498,174 B2 * | 11/2016 | Saha | A61B 6/4417 |
| 9,606,199 B2 * | 3/2017 | Breuer | G01R 33/28 |
| 9,696,398 B2 * | 7/2017 | Ryu | G01R 33/481 |
| 9,737,274 B2 * | 8/2017 | Bagamery | A61B 6/037 |
| 2007/0055127 A1 * | 3/2007 | Ladebeck | G01R 33/481 600/407 |
| 2007/0102641 A1 | 5/2007 | Schmand et al. | |
| 2008/0146914 A1 | 6/2008 | Polzin et al. | |
| 2008/0208035 A1 | 8/2008 | Nistler et al. | |
| 2008/0214927 A1 | 9/2008 | Cherry et al. | |
| 2008/0265887 A1 * | 10/2008 | Linz | G01R 33/28 324/318 |
| 2008/0284428 A1 | 11/2008 | Fiedler et al. | |
| 2008/0309341 A1 * | 12/2008 | Dooms | G01R 33/36 324/318 |
| 2009/0005671 A1 * | 1/2009 | Kreischer | A61B 6/037 600/411 |
| 2009/0299170 A1 | 12/2009 | Gebhardt et al. | |
| 2011/0018541 A1 | 1/2011 | Solf et al. | |
| 2011/0224534 A1 | 9/2011 | Yamaya et al. | |
| 2012/0150017 A1 | 6/2012 | Yamaya et al. | |

FOREIGN PATENT DOCUMENTS

| | | |
|---|---|---|
| JP | 2008-525161 | 7/2008 |
| JP | 2008-206977 | 9/2008 |
| JP | 2008-536600 | 9/2008 |
| JP | 2009-518098 | 5/2009 |
| WO | WO 2006/111869 A2 | 10/2006 |
| WO | 2008/129666 A1 | 10/2008 |
| WO | WO 2009/107005 | 9/2009 |
| WO | 2010/103644 A1 | 9/2010 |

OTHER PUBLICATIONS

Office Action dated Mar. 31, 2014 in CN 201180004171.6.
International Search Report for PCT/JP2011/074991, dated Dec. 27, 2011.
Catana, C. et al., "Simultaneous Acquisition of Multislice PET and MR Images: Initial Results with a MR-Compatible PET Scanner", The Journal of Nuclear Medicine, vol. 47, No. 12, (Dec. 2006), pp. 1968-1976.

* cited by examiner ial application Ser. No. PCT/JP2011/074991 filed on Oct. 28, 2011 which designates the United States, and which claims the benefit of priority from Japanese Patent Application No. 2010-245606, filed on Nov. 1, 2010; the entire contents of which are incorporated herein by reference.

PET-MRI APPARATUS

CROSS-REFERENCE TO RELATED APPLICATIONS

This application is a continuation of PCT international application Ser. No. PCT/JP2011/074991 filed on Oct. 28, 2011 which designates the United States, and which claims the benefit of priority from Japanese Patent Application No. 2010-245606, filed on Nov. 1, 2010; the entire contents of which are incorporated herein by reference.

FIELD

Embodiments described herein relate generally to a PET (Positron Emission Tomography)-MRI (Magnetic Resonance Imaging) apparatus.

BACKGROUND

In many cases, MRI apparatuses have been utilized to inspect cephalic regions, for example. It has been also expected that PET apparatuses are utilized to inspect cephalic regions, e.g., to diagnose Alzheimer diseases. Hence, recently, it has been expected to realize a PET-MRI apparatus combining a PET apparatus and an MRI apparatus.

The MRI apparatuses, however, have some limitations. For example, a photomultiplier tube (PMT) used as a detector of a conventional PET apparatus cannot be used when the PET-MRI apparatus is intended to be realized because a strong radio frequency magnetic field is used in the MRI apparatus. Therefore, a PET-MRI apparatus has been proposed that uses an APD (Avalanche Photodiode) or a SiPM (Silicon Photomultiplier) instead of the PMT, for example.

In some conventional PET-MRI apparatuses, a PET detector is disposed at the magnetic field center included in an effective imaging region of MR images. Such a disposition is the most suitable for taking PET images. However, in order to take MR images, this disposition is not always the most suitable because MR images having sufficient image quality are not obtained in some cases due to influence of material of the PET detector disposed around the magnetic field center.

DETAILED DESCRIPTION

A PET-MRI apparatus according to an embodiment includes a magnet, a transmitting radio frequency coil, a gradient coil, a receiving radio frequency coil, an MR image reconstruction unit, a first detector, and a PET image reconstruction unit. The magnet is configured to be a seamless structure and generate a static magnetic field in a bore having a cylindrical shape. The transmitting radio frequency coil is configured to apply a radio frequency pulse on a subject placed in the static magnetic field. The gradient coil is configured to apply a gradient magnetic field on the subject on which the radio frequency pulse is applied. The receiving radio frequency coil is configured to detect a magnetic resonance signal emitted from the subject due to application of the radio frequency pulse and the gradient magnetic field on the subject. The MR image reconstruction unit is configured to reconstruct an MR image based on the magnetic resonance signal detected by the receiving radio frequency coil. The first detector and a second detector are each configured to have a ring shape and detect gamma rays emitted from a positron emitting radionuclide injected into the subject. The PET image reconstruction unit is configured to reconstruct a PET image from projection data produced based on the gamma rays detected by the first and the second detectors. The first and the second detectors are disposed in an axial direction of the bore with a space therebetween so as to interpose a magnetic field center of the static magnetic field therebetween.

Embodiments of a PET-MRI apparatus are described in detail below with reference to the accompanying drawings.

First Embodiment

Figure 1:
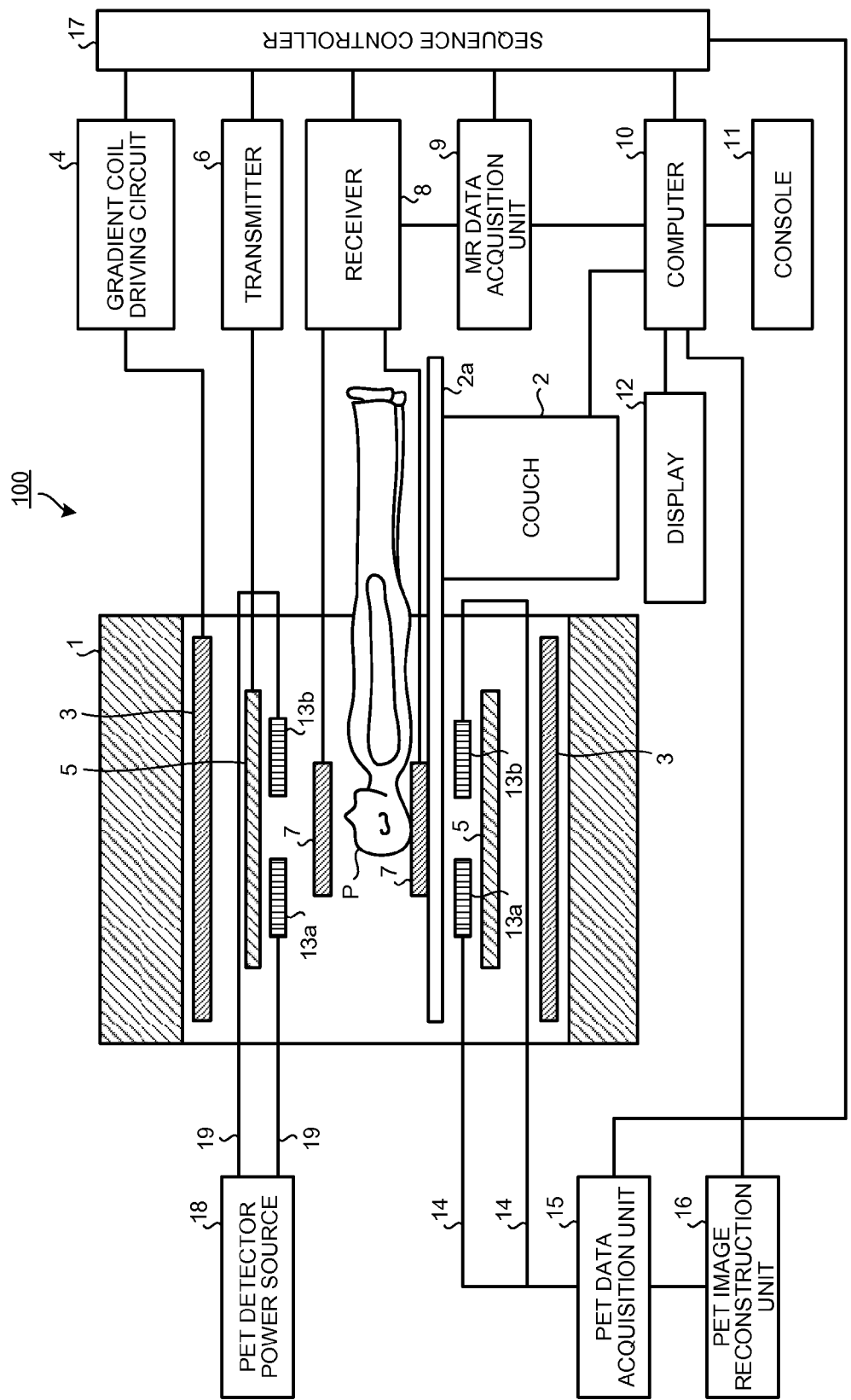
FIG. 1 is a schematic illustrating a structure of a PET-MRI apparatus according to a first embodiment.

First, a structure of a PET-MRI apparatus according to a first embodiment is described. FIG. 1 is a schematic illustrating a structure of a PET-MRI apparatus 100 according to the first embodiment. As illustrated in FIG. 1, the PET-MRI apparatus 100 includes a magnet 1, a couch 2, a gradient coil 3, a gradient coil driving circuit 4, a transmitting radio frequency coil 5, a transmitter 6, a receiving radio frequency coil 7, a receiver 8, an MR data acquisition unit 9, a computer 10, a console 11, a display 12, PET detectors 13a and 13b, signal lines 14, a PET data acquisition unit 15, a PET image reconstruction unit 16, a sequence controller 17, a PET detector power source 18, and power source cables 19.

The magnet 1, which is a seamless structure, generates a static magnetic field in a bore having an approximately cylindrical shape. The bore is formed as the inner surface of a gantry having an approximately cylindrical shape and housing the magnet 1, the gradient coil 3, and the like. The couch 2 has a couchtop 2a on which a subject P is placed. When the subject P is imaged, the couch 2 moves the couchtop 2a into an inside of the bore, so that the subject P is moved in the static magnetic field.

The gradient coil 3 applies gradient magnetic fields Gx, Gy, and Gz on the subject P. The magnetic field intensities of the gradient magnetic fields Gx, Gy, and Gz in the same direction (Z direction) as the static magnetic field change linearly in relation to the distance from the magnetic field center in the X, Y, and Z directions, respectively. The gradient coil 3 is formed in an approximately cylindrical shape and disposed on a side adjacent to an inner circumference of the magnet 1. The gradient coil driving circuit 4 drives the gradient coil 3 under control of the sequence controller 17.

The transmitting radio frequency coil 5 applies a radio frequency magnetic field on the subject P placed in the static magnetic field based on a radio frequency pulse transmitted from the transmitter 6. The transmitting radio frequency coil 5 is formed in an approximately cylindrical shape and disposed on a side adjacent to an inner circumference of the gradient coil 3. The transmitter 6 transmits the radio frequency pulse to the transmitting radio frequency coil 5 under control of the sequence controller 17.

The receiving radio frequency coil 7 detects a magnetic resonance signal emitted from the subject P due to the application of the radio frequency magnetic field and the gradient magnetic field on the subject P. For example, the receiving radio frequency coil 7 is a surface coil disposed on a surface of the subject P corresponding to a region to be imaged. For example, when a body region of the subject P is imaged, two receiving radio frequency coils 7 are disposed on the upper side and the lower side of the subject P. The receiver 8 receives the magnetic resonance signal detected by the receiving radio frequency coil 7 under control of the sequence controller 17. The receiver 8 transmits the received magnetic resonance signal to the MR data acquisition unit 9.

The MR data acquisition unit 9 acquires the magnetic resonance signal sent from the receiver 8 under control of the sequence controller 17. The MR data acquisition unit 9 amplifies the acquired magnetic resonance signal and performs detection on the amplified signal. Thereafter, the MR data acquisition unit 9 A/D-converts the signal after the detection and sends the converted signal to the computer 10. The computer 10, which is controlled with the console 11, reconstructs an MR image based on the magnetic resonance signal sent from the MR data acquisition unit 9. The computer 10 allows the display 12 to display the reconstructed MR image.

The PET detectors 13a and 13b detect, as counting information, gamma rays emitted from positron emitting radionuclides injected into the subject P. The PET detectors 13a and 13b are each formed in a ring shape and disposed on a side adjacent to an inner circumference of the transmitting radio frequency coil 5. For example, the PET detectors 13a and 13b are each formed by arranging detector modules including scintillators and photo detectors in a ring shape. Examples of the scintillator include LYSO (Lutetium Yttrium Oxyorthosilicate), LSO (Lutetium Oxyorthosilicate), and LGSO (Lutetium Gadolinium Oxyorthosilicate). The photo detector is, for example, a semiconductor detector such as an APD (Avalanche Photodiode) element and a SiPM (Silicon Photomultiplier). The PET detectors 13a and 13b send the detected counting information to the PET data acquisition unit 15 through the signal lines 14.

The PET data acquisition unit 15 produces simultaneous counting information under control of the sequence controller 17. The PET data acquisition unit 15 produces, as the simultaneous counting information, a combination of counting information of gamma rays (including annihilation radiation) that are emitted from the positron emitting radionuclides and approximately simultaneously detected by using the counting information of the gamma rays detected by the PET detectors 13a and 13b.

The PET image reconstruction unit 16 reconstructs a PET image by using the simultaneous counting information produced by the PET data acquisition unit 15 as projection data. The PET image reconstructed by the PET image reconstruction unit 16 is transmitted to the computer 10 and displayed on the display 12. The sequence controller 17 controls the above-described elements based on various imaging sequences executed when the subject is imaged. The PET detector power source 18 supplies the PET detectors 13a and 13b with power to drive the photo detectors through the power source cables 19.

Figure 2:
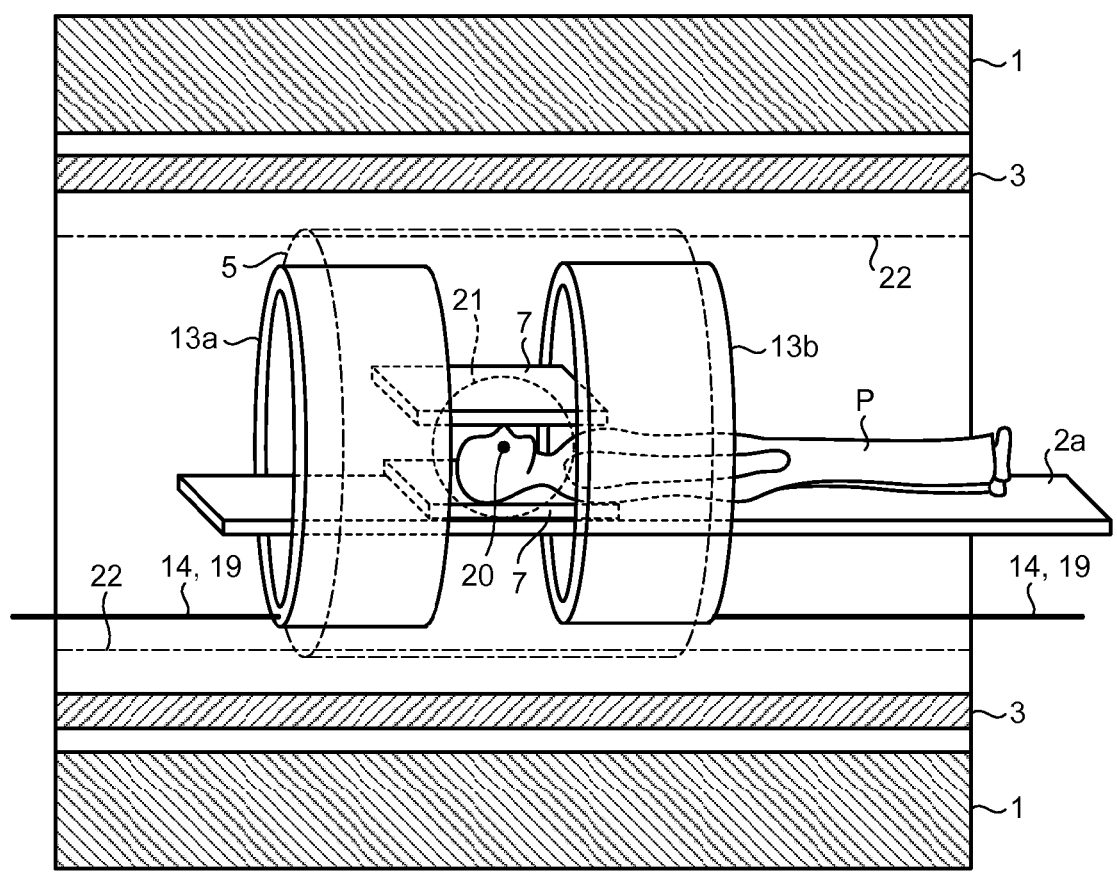
FIG. 2 is a schematic illustrating an element arrangement at a periphery of a PET detector according to the first embodiment.

An element arrangement at a periphery of the PET detectors 13a and 13b is described below. FIG. 2 is a schematic illustrating the element arrangement at the periphery of the PET detectors 13a and 13b according to the first embodiment. A dot 20 illustrated in FIG. 2 represents the magnetic field center of the static magnetic field. A region 21 surrounded with the dashed line in FIG. 2 represents an effective imaging region of the MR image.

As illustrated in FIG. 2, the PET detectors 13a and 13b are disposed on a side adjacent to an inner circumference of a bore 22 in the first embodiment. The PET detectors 13a and 13b are disposed with a space therebetween in an axial direction of the bore 22 so as to interpose the magnetic field center 20 of the static magnetic field generated by the magnet 1 therebetween. That is, in the first embodiment, the PET detectors 13a and 13b are disposed so as to avoid the periphery of the magnetic field center included in the effective imaging region of the MR image. As a result, deterioration of image quality of the MR image due to the influence of the PET detectors is suppressed.

In addition, the signal lines 14 and the power source cables 19 that are connected to the PET detectors 13a and 13b are routed so as not to pass through the periphery of the magnetic field center 20 of the static magnetic field generated by the magnet 1. For example, as illustrated in FIG. 2, the signal line 14 and the power source cable 19 that are connected to the PET detector 13a are combined and routed from the PET detector 13a to a side opposite the magnetic field center 20. Likewise, the signal line 14 and the power source cable 19 that are connected to the PET detector 13b are combined and routed from the PET detector 13b to a side opposite the magnetic field center 20. The signal line 14 and the power source cable 19 may be combined with cables connected to the transmitting radio frequency coil 5 and routed, for example.

The PET detectors 13a and 13b each converts a signal relating to the detected gamma rays from an analog signal to a digital signal, thereafter further converts the digital signal into an optical signal, and outputs the optical signal. The PET detectors 13a and 13b each may convert a signal relating to the detected gamma rays from an analog signal to a digital signal, thereafter further convert the digital signal into a radio signal, and outputs the radio signal. In this way, signals output from the PET detectors 13a and 13b are converted into optical signals or radio signals. As a result, noises caused by the digital signals can be prevented.

Figure 3:
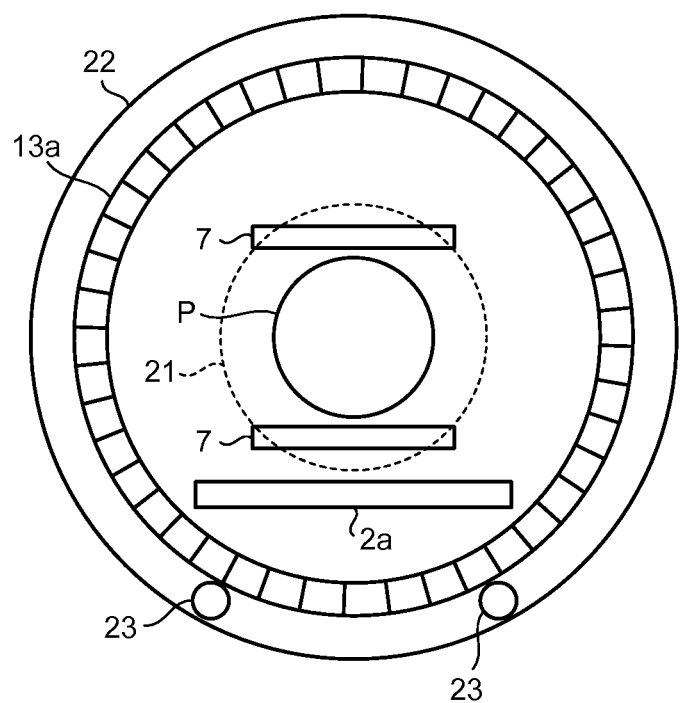
FIG. 3 is a schematic illustrating the element arrangement at the periphery of the PET detector according to the first embodiment when viewed from an axial direction of a bore.

The PET-MRI apparatus 100 includes a moving mechanism that moves the PET detectors 13a and 13b along the axial direction of the bore 22. FIG. 3 is a schematic illustrating the element arrangement at the periphery of the PET detectors 13a and 13b according to the first embodiment when viewed from the axial direction of the bore 22. FIG. 3 illustrates the element arrangement when the inside of the bore is viewed from an opening on a side on which the PET detector 13a is disposed.

As illustrated in FIG. 3, a moving mechanism 23 is two rails disposed on the internal surface of the bore 22 at the lower side, for example. For example, the moving mechanism 23 is engaged with a rail engagement portion formed in a groove shape on the outer circumference surface of the PET detector 13a and supports the PET detector 13a so as to be movable along the axial direction of the bore 22.

Likewise, the moving mechanism 23 to move the PET detector 13b is provided on the PET detector 13b.

The PET detectors 13a and 13b can be attachable to and detachable from the corresponding moving mechanism 23, so that they can be inserted in and removed from the bore 22 by passing through both sides of the bore 22. The structure allowing the PET detectors 13a and 13b to be attachable and detachable enables the PET detectors 13a and 13b to be relatively easily built in a conventional MRI apparatus, allowing the PET-MRI apparatus to be widely popularized.

The moving mechanism 23 moves the PET detectors 13a and 13b based on imaging modes under control of the computer 10. For example, the moving mechanism 23 automatically moves the PET detectors 13a and 13b based on an imaging condition that the computer 10 receives from an operator. Alternatively, the moving mechanism 23 may move the PET detectors 13a and 13b based on a movement instruction input by an operator through the console 11.

As a specific example, when an imaging mode is executed in which the PET image and the MR image are taken simultaneously, the moving mechanism 23 moves the PET detectors 13a and 13b to a position at which they interpose the magnetic field center 20 of the static magnetic field therebetween before imaging starts. As another example, when an imaging mode is executed in which only the PET image is taken, the moving mechanism 23 moves the PET detectors 13a and 13b so as to be adjacent to each other before imaging starts. As still another example, when an imaging mode is executed in which only the MR image is taken, the moving mechanism 23 moves the PET detectors 13a and 13b out of the static magnetic field.

For example, the moving mechanism 23 moves the PET detectors 13a and 13b based on the imaging condition for taking the PET image and/or the imaging condition for taking the MR image. For example, when moving the PET detectors 13a and 13b, the moving mechanism 23 changes the distance between the PET detectors 13a and 13b after being moved based on a size of an FOV (Field Of View) set as the imaging condition for taking the MR image and a type of the receiving radio frequency coil 7.

Figure 4:
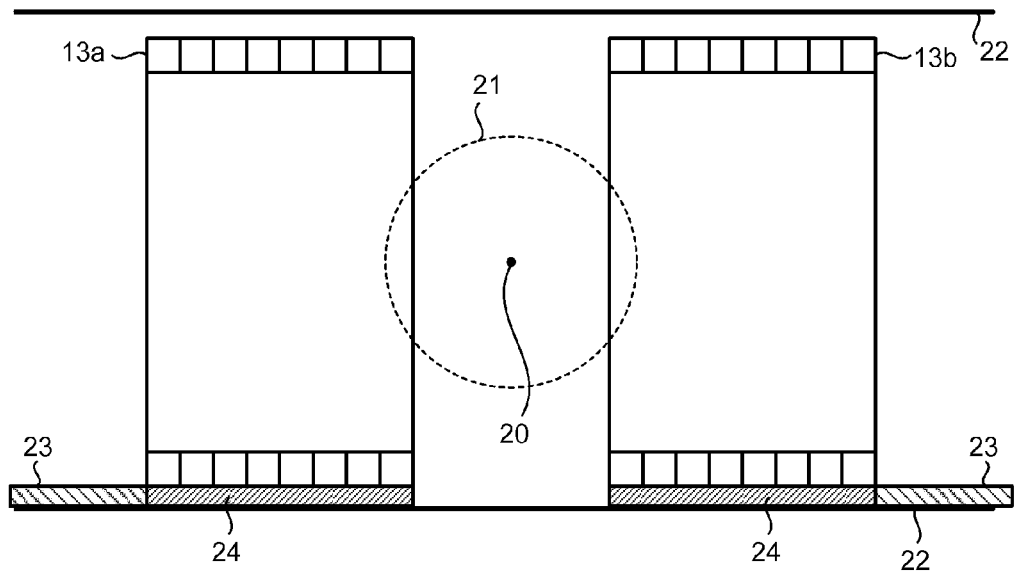
FIG. 4 is a schematic illustrating a vibration damping mechanism according to the first embodiment.

The PET-MRI apparatus 100 includes a vibration damping mechanism that fixes a position of each PET detector after the PET detectors 13a and 13b are moved to an imaging position by the moving mechanism 23 and damps vibration transmitted from the gradient coil 3 to each PET detector. FIG. 4 is a schematic illustrating a vibration damping mechanism 24 according to the first embodiment. As illustrated in FIG. 4, the vibration damping mechanism 24 is disposed at an engaged portion between the PET detector 13a and the moving mechanism 23, for example. Likewise, the vibration damping mechanism 24 is disposed at an engaged portion between the PET detector 13b and the moving mechanism 23.

Figure 5:
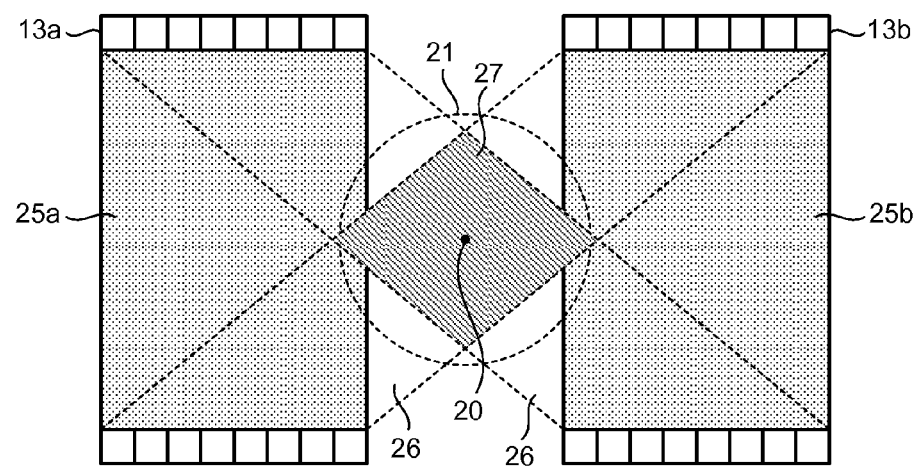
FIG. 5 is a schematic illustrating an effective imaging region of the PET-MRI apparatus according to the first embodiment.

The effective imaging region of the PET-MRI apparatus 100 according to the first embodiment is described below. FIG. 5 is a schematic illustrating the effective imaging region of the PET-MRI apparatus 100 according to the first embodiment. As illustrated in FIG. 5, in the PET-MRI apparatus 100, a region 25a surrounded by the inner circumference surface of the PET detector 13a and a region 25b surrounded by the inner circumference surface of the PET detector 13b are the effective imaging region in which only the PET image can be taken.

In addition, as illustrated in FIG. 5, a region 27 that is included in both of a region 26 formed between the inner circumference surface of the PET detector 13a and the inner circumference surface of the PET detector 13b and the effective imaging region 21 of the MR image is the effective imaging region in which the PET image and the MR image can be taken simultaneously. The effective imaging region 27 has a shape obtained by bonding the bottoms of circular cones each other.

In this way, in the PET-MRI apparatus 100 according to the first embodiment, the effective imaging region 21 in which the MR image can be taken, the effective imaging regions 25a and 25b in which the PET image can be taken, and the effective imaging region 27 in which the MR image and the PET image can be simultaneously taken are set.

As described above, the PET-MRI apparatus 100 according to the first embodiment includes the magnet 1, the transmitting radio frequency coil 5, the gradient coil 3, the receiving radio frequency coil 7, the computer 10, the PET detectors 13a and 13b, and the PET image reconstruction unit 16. The magnet 1, which is the seamless structure, generates the static magnetic field in the bore 22 having a cylindrical shape. The transmitting radio frequency coil 5 applies the radio frequency pulse on the subject P placed in the static magnetic field. The gradient coil 3 applies the gradient magnetic field on the subject P on which the radio frequency pulse is applied. The receiving radio frequency coil 7 detects the magnetic resonance signal emitted from the subject P due to the application of the radio frequency pulse and the gradient magnetic field on the subject P. The computer 10 reconstructs the MR image based on the magnetic resonance signal detected by the receiving radio frequency coil 7. The PET detectors 13a and 13b are each formed in a ring shape and detect gamma rays emitted from positron emitting radionuclides injected into the subject P. The PET image reconstruction unit 16 reconstructs the PET image from projection data produced based on the gamma rays detected by the PET detectors 13a and 13b. The PET detectors 13a and 13b are disposed with a space therebetween in the axial direction of the bore 22 so as to interpose the magnetic field center 20 of the static magnetic field therebetween. In this way, in the first embodiment, the PET detectors 13a and 13b are disposed so as to avoid the periphery of the magnetic field center included in the effective imaging region of the MR image. As a result, according to the first embodiment, deterioration of image quality of the MR image due to the influence of the PET detectors can be suppressed.

In the first embodiment, the PET detectors 13a and 13b are disposed on the side adjacent to the inner circumference of the transmitting radio frequency coil 5. As a result, the PET detectors 13a and 13b can be easily added to a conventional MRI apparatus having an imaging space on the side adjacent to the inner circumference of the transmitting radio frequency coil 5, allowing the PET-MRI apparatus to be easily realized.

In the first embodiment, the moving mechanism 23 moves the PET detectors 13a and 13b along the axial direction of the bore 22 based on the imaging modes. As a result, when both or one of the PET image and the MR image is taken, the PET detectors 13a and 13b can be moved to a proper position based on the type of imaging to be executed.

In the first embodiment, when the imaging mode is executed in which the PET image and the MR image are taken simultaneously, the moving mechanism 23 moves the PET detectors 13a and 13b to the position at which they interpose the magnetic field center 20 of the static magnetic field therebetween before imaging starts. As a result, when the PET image and the MR image are imaged simultaneously, the MR image having high quality can be easily taken.

In the first embodiment, when the imaging mode is executed in which only the PET image is taken, the moving mechanism 23 moves the PET detectors 13a and 13b so as to be adjacent to each other before imaging starts. As a result, when only the PET image is taken, a wider imaging region can be provided.

In the first embodiment, when the imaging mode is executed in which only the MR image is taken, the moving mechanism 23 moves the PET detectors 13a and 13b out of the static magnetic field. As a result, when only the MR image is taken, the MR image can be obtained that has no deterioration of image quality due to the PET detectors 13a and 13b.

In the first embodiment, the moving mechanism 23 moves the PET detectors 13a and 13b based on the imaging condition for taking the PET image and/or the imaging condition for taking the MR image. As a result, when both or one of the PET image and the MR image is taken, the distance between the PET detectors 13a and 13b can be automatically set.

In the first embodiment, the vibration damping mechanism 24 fixes the position of each PET detector after the PET detectors 13a and 13b are moved to the imaging position by the moving mechanism 23 and damps vibration transmitted from the gradient coil 3 to each PET detector. As a result, the PET detectors 13a and 13b can be protected from mechanical vibration caused by the gradient coil 3.

In the first embodiment, the signal lines 14 and the power source cables 19 that are connected to the PET detectors 13a and 13b are routed so as not to pass through the periphery of the magnetic field center 20 of the static magnetic field. As a result, noises generated by the signals output from the PET detectors 13a and 13b can be suppressed.

In the first embodiment, the PET detectors 13a and 13b each converts a signal relating to the detected gamma rays from an analog signal to a digital signal, thereafter further converts the digital signal into an optical signal, and outputs the optical signal. As a result, noises generated by the signals output from the PET detectors 13a and 13b can be more reliably suppressed.

In the first embodiment, the PET detectors 13a and 13b each converts a signal relating to the detected gamma rays from an analog signal to a digital signal, thereafter further converts the digital signal into a radio signal, and outputs the radio signal. As a result, noises generated by the signals output from the PET detectors 13a and 13b can be more reliably suppressed.

Second Embodiment

A second embodiment is described below. In the first embodiment, the PET detectors 13a and 13b are disposed on the side adjacent to the inner circumference of the transmitting radio frequency coil 5. In contrast, in the second embodiment, PET detectors 33a and 33b are disposed on a side adjacent to the outer circumference of the transmitting radio frequency coil 5. The basic structure of a PET-MRI apparatus according to the second embodiment is the same as that illustrated in FIG. 1 but only the PET detectors 33a and 33b are arranged in a different manner from those illustrated in FIG. 1.

Figure 6:
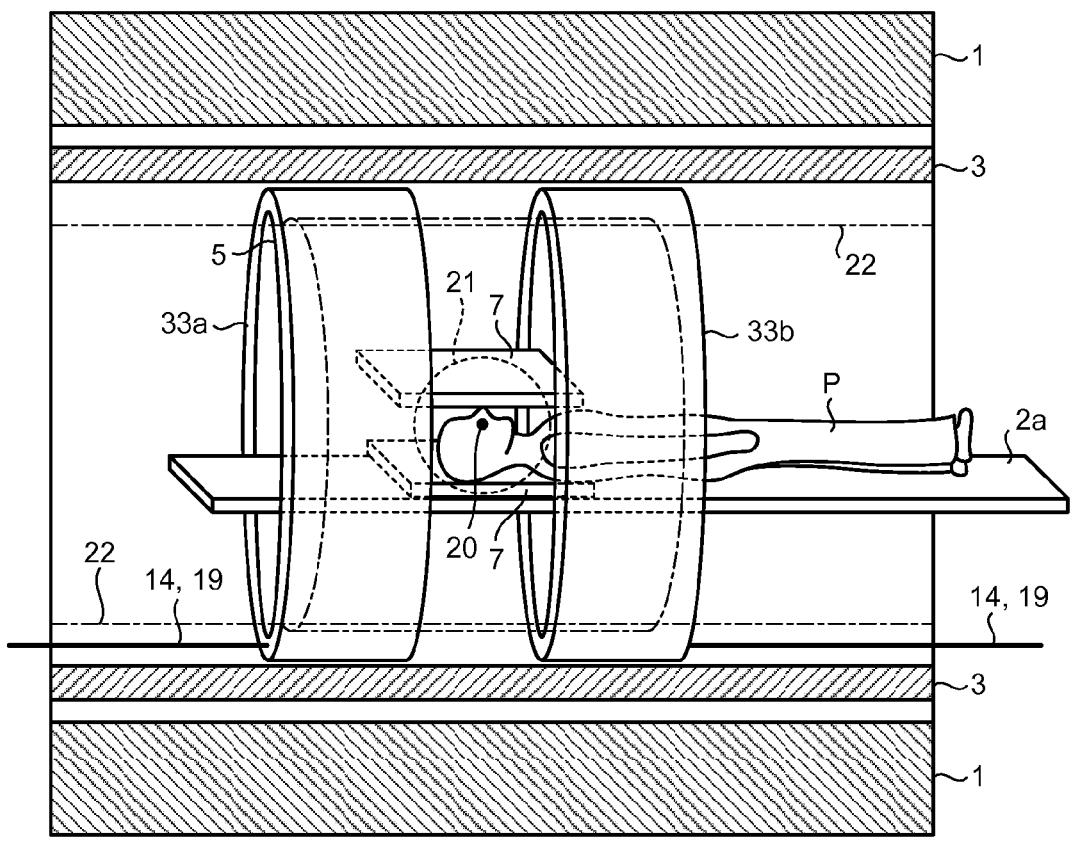
FIG. 6 is a schematic illustrating an element arrangement at a periphery of a PET detector according to a second embodiment.

FIG. 6 is a schematic illustrating the element arrangement at the periphery of the PET detectors 33a and 33b according to the second embodiment. The elements having the same function as the elements of FIG. 2 are labeled with the same numerals, and detailed description thereof is omitted. As illustrated in FIG. 6, the PET detectors 33a and 33b are disposed on the side adjacent to the outer circumference of the transmitting radio frequency coil 5 in the second embodiment. For example, this structure is used for imaging a body region by using the transmitting radio frequency coil 5 as a whole-body transmission RF coil and the receiving radio frequency coil 7 as a dedicated surface coil for the body region.

In the structure, the PET detectors 33a and 33b are fixedly disposed at the position so as to interpose the magnetic field center of the static magnetic field therebetween. The PET detectors 33a and 33b may be fixed to the apparatus with the vibration damping mechanism that damps vibration generated by the gradient coil 3 interposed therebetween in the same manner as the first embodiment. For example, the PET detectors 33a and 33b are fixed to the inner circumference surface of the gradient coil 3 with the vibration damping mechanism interposed therebetween. As a result, the PET detectors 33a and 33b can be protected from mechanical vibration caused by the gradient coil 3 also in the second embodiment.

In this way, also in the second embodiment, the PET detectors 33a and 33b are disposed so as to avoid the periphery of the magnetic field center included in the effective imaging region of the MR image. As a result, according to the second embodiment, deterioration of image quality of the MR image due to the influence of the PET detectors can be suppressed in the same manner as the first embodiment.

Third Embodiment

A third embodiment is described below. In the third embodiment, imaging is repeated while the couchtop 2a on which the subject P is placed is moved step-by-step in the axial direction of the bore 22 in the PET-MRI apparatus described in the first or the second embodiment. Such an imaging method is called a step-and-shoot. Herein, a case is described in which the step-and-shoot is performed in the PET-MRI apparatus described in the first embodiment.

Figure 7:
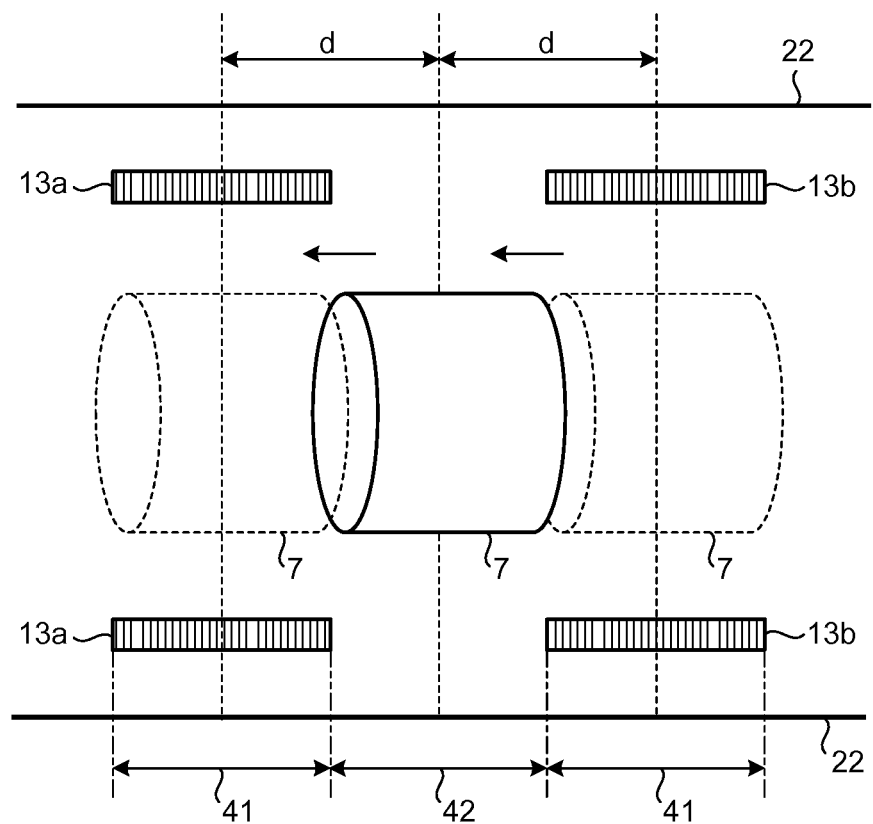
FIG. 7 is a schematic to explain a step-and-shoot according to a third embodiment.

FIG. 7 is a schematic to explain the step-and-shoot according to the third embodiment. In the step-and-shoot according to the third embodiment, the couch 2 moves the couchtop 2a, so that the subject P is moved along the axial direction of the bore 22. The computer 10 controls the couch 2 such that a region to be imaged of the subject P is moved step-by-step in the order of an approximate center position of the PET detector 13b, an approximate center position of a region interposed between the PET detectors 13a and 13b, and an approximate center position of the PET detector 13a.

As a result, as illustrated in FIG. 7, the receiving radio frequency coil 7 attached on the imaging position of the subject P is moved step-by-step. Specifically, the receiving radio frequency coil 7 is moved in the axial direction of the bore 22 step-by-step by a distance d that is half of the distance between the centers of the PET detectors 13a and 13b. As a result, the region to be imaged is moved in the axial direction of the bore 22 in the order of a range 41 in which only the PET image can be taken, a range 42 in which the MR image and the PET image can be taken simultaneously, and the range 41 in which only the PET image can be taken.

For example, the computer 10 controls the PET-MRI apparatus 100 so as to take the PET image when the region to be imaged is moved to the approximate center position of the PET detector 13a or the approximate center position of the PET detector 13b. The computer 10 controls the PET-MRI apparatus 100 so as to take both or one of the PET image and the MR image when the region to be imaged is moved to the approximate center position of the region interposed between the PET detectors 13a and 13b. In this way, the PET image and both or one of the PET image and the MR image can be taken in the order while the region to be imaged is moved step-by-step. Also in the third embodiment, the deterioration of image quality of the MR image due to the influence of the PET detectors can be suppressed in the same manner as the first and the second embodiments.

In the first to the third embodiments, the PET detectors 13a and 13b, i.e., two PET detectors, are disposed. However, the embodiment of the PET-MRI apparatus is not limited to this arrangement. For example, the number of PET detectors may be three or more. That is, even when more than two of the PET detectors 13a and 13b are disposed, the PET image and the MR image can be taken simultaneously in the region interposed between the PET detectors.

As described above, according to the first, the second, or the third embodiment, the PET-MRI apparatus can be realized that can suppress the deterioration of image quality of the MR image due to the influence of the PET detectors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A PET (Positron Emission Tomography)-MRI (Magnetic Resonance Imaging) apparatus, comprising:
    a magnet configured to be a seamless structure and generate a static magnetic field in a bore having a cylindrical shape;
    a transmitting radio frequency coil configured to apply a radio frequency pulse on a subject placed in the static magnetic field;
    a gradient coil configured to apply a gradient magnetic field on the subject on which the radio frequency pulse is applied;
    a receiving radio frequency coil configured to detect a magnetic resonance signal emitted from the subject due to application of the radio frequency pulse and the gradient magnetic field on the subject;
    an MR image reconstruction unit configured to reconstruct an MR image based on the magnetic resonance signal detected by the receiving radio frequency coil;
    a first detector and a second detector each configured to have a ring shape and detect gamma rays emitted from a positron emitting radionuclide injected into the subject; and
    a PET image reconstruction unit configured to reconstruct a PET image from projection data produced based on the gamma rays detected by the first and the second detectors, wherein
    the first and the second detectors are spaced apart in an axial direction of the bore with the space therebetween encompassing a center of the static magnetic field.

2. The PET-MRI apparatus according to claim 1, wherein the first and the second detectors are disposed on a side adjacent to an inner circumference of the transmitting radio frequency coil.

3. The PET-MRI apparatus according to claim 1, wherein the first and the second detectors are disposed on a side adjacent to an outer circumference of the transmitting radio frequency coil.

4. The PET-MRI apparatus according to claim 1, further comprising a moving unit configured to move the first and the second detectors along the axial direction of the bore based on an imaging mode.

5. The PET-MRI apparatus according to claim 4, wherein the moving unit moves the first and the second detectors to a position at which the detectors interpose the magnetic field center of the static magnetic field therebetween before imaging starts when the imaging mode in which the PET image and the MR image are simultaneously taken is executed.

6. The PET-MRI apparatus according to claim 4, wherein the moving unit moves the first and the second detectors so as to be adjacent to each other before imaging starts when the imaging mode in which only the PET image is taken is executed.

7. The PET-MRI apparatus according to claim 4, wherein the moving unit moves the first and the second detectors out of the static magnetic field when the imaging mode in which only the MR image is taken is executed.

8. The PET-MRI apparatus according to claim 4, wherein the moving unit moves the first and the second detectors based on an imaging condition for taking the PET image and/or an imaging condition for taking the MR image.

9. The PET-MRI apparatus according to claim 4, further comprising a vibration damping unit configured to fix a position of each detector after the first and the second detectors are moved to an imaging position by the moving unit and damp vibration transmitted from the gradient coil to each detector.

10. The PET-MRI apparatus according to claim 1, wherein the first and the second detectors are fixedly disposed at a position at which the detectors interpose the magnetic field center of the static magnetic field therebetween.

11. The PET-MRI apparatus according to claim 10, wherein the first and the second detectors are fixed to the apparatus with a vibration damping unit that damps vibration generated by the gradient coil interposed therebetween.

12. The PET-MRI apparatus according to claim 1, wherein signal lines and power source lines that are connected to the first and the second detectors are routed so as not to pass through a periphery of the magnetic field center of the static magnetic field.

13. The PET-MRI apparatus according to claim 1, wherein the first and the second detectors each convert a signal relating to the detected gamma rays from an analog signal to a digital signal, further convert the digital signal to an optical signal, and output the optical signal.

14. The PET-MRI apparatus according to claim 1, wherein the first and the second detectors each convert a signal relating to the detected gamma rays from an analog signal to a digital signal, further convert the digital signal to a radio signal, and output the radio signal.

15. The PET-MRI apparatus according to claim 1, further comprising:
    a couch configured to move a couchtop on which the subject is placed along the axial direction of the bore; and
    a controller configured to control the couch such that a region to be imaged is moved to an approximate center position of the first detector, an approximate center position of a region interposed between the first and the second detectors, and an approximate center position of the second detector step-by-step, control the apparatus so as to take both or one of the MR image and the PET image when the region to be imaged is moved to the approximate center position of the first detector or the second detector, and control the apparatus so as to take the PET image when the region to be imaged is moved to the approximate center position of the region interposed between the first and the second detectors.

* * * * *

UNITED STATES PATENT AND TRADEMARK OFFICE
CERTIFICATE OF CORRECTION

PATENT NO. : 9,880,236 B2
APPLICATION NO. : 13/874795
DATED : January 30, 2018
INVENTOR(S) : Obata et al.

It is certified that error appears in the above-identified patent and that said Letters Patent is hereby corrected as shown below:

On the Title Page

(71) Applicants should read: NATIONAL INSTITUTES FOR QUANTUM AND RADIOLOGICAL SCIENCE AND TECHNOLOGY, Chiba (JP); TOSHIBA MEDICAL SYSTEMS CORPORATION, Otawara-shi Tochigi (JP)

Signed and Sealed this
Tenth Day of April, 2018

Andrei Iancu
*Director of the United States Patent and Trademark Office*